United States Patent
Huh et al.

(10) Patent No.: US 9,477,096 B2
(45) Date of Patent: Oct. 25, 2016

(54) OPTICAL-CHARACTERISTICS ADJUSTING SYSTEM FOR SUNGLASSES OR GOGGLES AND SUNGLASSES AND GOGGLES EQUIPPED THEREWITH

(75) Inventors: Moon-Young Huh, Seoul (KR); Sung-Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 267 days.

(21) Appl. No.: 13/880,797

(22) PCT Filed: Sep. 9, 2011

(86) PCT No.: PCT/KR2011/006745
§ 371 (c)(1),
(2), (4) Date: Apr. 22, 2013

(87) PCT Pub. No.: WO2012/053744
PCT Pub. Date: Apr. 26, 2012

(65) Prior Publication Data
US 2013/0222710 A1    Aug. 29, 2013

(30) Foreign Application Priority Data
Oct. 22, 2010    (KR) .......................... 10-2010-0103341

(51) Int. Cl.
*G02C 7/10*   (2006.01)
*G02C 7/02*   (2006.01)
(Continued)

(52) U.S. Cl.
CPC ................. *G02C 7/02* (2013.01); *A61F 9/022* (2013.01); *G02C 7/10* (2013.01); *G02C 7/101* (2013.01); *G02C 7/107* (2013.01); *G02C 7/108* (2013.01); *G02C 11/10* (2013.01); *G02F 1/13318* (2013.01)

(58) Field of Classification Search
CPC .......... G02C 7/10; G02C 7/107; G02C 7/108
See application file for complete search history.

(56) References Cited

U.S. PATENT DOCUMENTS 6,097,450 A * 8/2000 Humphrey ...................... 349/13
6,350,275 B1 * 2/2002 Vreman et al. ................. 607/88
(Continued)

FOREIGN PATENT DOCUMENTS

| JP | 06-043405 A | 2/1994 |
| JP | 08-136883 A | 5/1996 |

(Continued)

OTHER PUBLICATIONS

International Search Report (in Korean and English) for PCT/KR2011/006745, mailed Apr. 19, 2012; ISA/KR.

*Primary Examiner* — Richard Kim
*Assistant Examiner* — Kendrick Hsu
(74) *Attorney, Agent, or Firm* — Harness, Dickey & Pierce, PLC (57) ABSTRACT

The present invention relates to sunglasses and goggles, and more particularly relates to a system for adjusting optical characteristics such as the color or the optical transmittance of sunglasses or goggles lens and relates to sunglasses and goggles equipped with the adjusting system. Provided is an optical characteristics adjusting system for sunglasses or goggles lenses, the system comprising: lenses equipped with an LCD panel; a lens drive unit equipped with an LCD drive unit for applying a driving voltage to the LCD panel; an illuminance detecting sensor for sensing the ambient illuminance; and a control unit for controlling the action of the lens drive unit in response to a signal from the illuminance detecting sensor. Also provided are sunglasses and goggles equipped with the optical characteristics adjusting system.

16 Claims, 8 Drawing Sheets (51) Int. Cl.
*A61F 9/02* (2006.01)
*G02C 11/00* (2006.01)
*G02F 1/133* (2006.01)

(56) References Cited

U.S. PATENT DOCUMENTS

2003/0231293 A1* 12/2003 Blum et al. .................. 356/5.01
2008/0062338 A1* 3/2008 Herzog ................. G02C 7/101
　　　　　　　　　　　　　　　　　　　349/13
2009/0147215 A1* 6/2009 Howell .................. G02C 11/00
　　　　　　　　　　　　　　　　　　　351/158
2010/0177277 A1* 7/2010 Kokonaski ............. G02C 7/083
　　　　　　　　　　　　　　　　　　　351/159.39
2011/0181828 A1* 7/2011 Yi et al. .......................... 351/47

FOREIGN PATENT DOCUMENTS

JP　　　09-179075 A　　　7/1997
JP　　　2008-181064 A　　　8/2008

* cited by examiner

OPTICAL-CHARACTERISTICS ADJUSTING SYSTEM FOR SUNGLASSES OR GOGGLES AND SUNGLASSES AND GOGGLES EQUIPPED THEREWITH

CROSS-REFERENCE TO RELATED APPLICATIONS

This application is a 371 U.S. National Stage of International Application No. PCT/KR2011/006745, filed on Sep. 9, 2011, which claims priority to Korean Patent Application No. 10-2010-0103341, filed on Oct. 22, 2010, the contents of which are hereby incorporated by reference in their entirety as if fully set forth herein.

TECHNICAL FIELD

The present invention relates to sunglasses and goggles, and more particularly, to a system for adjusting optical characteristics such as color, light transmissivity, or the like of a sunglasses or goggles lens, and sunglasses and goggles equipped therewith.

BACKGROUND ART

In the related art, in order to improve optical characteristics of sunglasses, a technique of using a discoloration lens configured to react with ultraviolet light or a liquid crystal configured to simply vary transmissivity has been proposed. However, when the discoloration lens is used, the discoloration lens cannot be easily used at night or in a vehicle in which an ultraviolet light shielding glass is installed, and is largely affected by a temperature in a use environment. In addition, in the case of the technique of using the liquid crystal for the purpose of simple transmissivity adjustment, use of the technique is limited because the technique cannot deal with surrounding illuminance. Accordingly, improved sunglasses and goggles capable of easily adjusting various optical characteristics according to variations in environments are needed.

DISCLOSURE

Technical Problem

In order to solve the foregoing and/or other problems, it is an aspect of the present invention to provide an optical characteristics adjusting system for sunglasses or goggles and sunglasses and goggles equipped therewith.

It is another aspect of the present invention to provide an optical characteristics adjusting system capable of adjusting an optical transmittance and/or color of sunglasses or goggles lenses and sunglasses and goggles lenses equipped therewith.

It is still another aspect of the present invention to provide an optical characteristics adjusting system capable of optimally and rapidly adjusting optical transmittance of sunglasses or goggles lenses according to surrounding temperature and illuminance and sunglasses and goggles equipped therewith.

It is yet still another aspect of the present invention to provide an optical characteristics adjusting system for sunglasses or goggles capable of minimizing power consumption and sunglasses and goggles equipped therewith.

It is further still another aspect of the present invention to provide an optical characteristics adjusting system capable of selecting automatic adjustment and manual adjustment of the optical transmittance of sunglasses or goggles lenses and sunglasses and goggles equipped therewith.

Technical Solution

The foregoing and/or other aspects of the present invention may be achieved by providing an optical characteristics adjusting system for sunglasses or goggles including a lens having an LCD panel; a lens drive unit having an LCD drive unit for applying a drive voltage to the LCD panel; an illuminance detecting sensor for detecting an ambient illuminance; and a control unit for controlling an operation of the lens drive unit according to a signal from the illuminance detecting sensor.

The LCD panel may be a shutter LCD having the optical transmittance adjusted by the LCD drive unit.

The optical characteristics adjusting system for sunglasses or goggles may further include a light source drive unit for emitting light having one or more colors, the lens may further include a diffusion color filter for receiving light from the light source drive unit, and the lens drivie unit may include a light source drive unit for driving the light source drive unit.

The lens may include a first LCD panel, which is red, a second LCD panel, which is green, and a third LCD panel, which is blue, and the LCD drive unit may include an electric current flowing time adjusting unit for adjusting an electric current flowing time of signals periodically output to the three LCD panels, and a distribution ratio manipulation unit for adjusting a distribution ratio of the signals output to the three LCD panels.

The optical characteristics adjusting system for sunglasses or goggles may further include a temperature detecting sensor for providing an ambient temperature data to the control unit, and the control unit may output the control signal compensated with respect to the ambient temperature to the LCD drive unit.

The optical characteristics adjusting system for sunglasses or goggles may further include a wearing detecting sensor for providing information about a wearing state of the sunglasses to the control unit.

The drive voltage of the LCD panel may have a frequency of 36 Hz or less.

The drive voltage of the LCD panel may have a frequency of 1 Hz or less.

The optical characteristics adjusting system for sunglasses or goggles may further include a function selection unit for selecting automatic adjustment and manual adjustment of optical transmittance of the lens.

In addition, another aspect of the present invention may be achieved by providing sunglasses and goggles equipped with the optical characteristics adjusting system.

Advantageous Effects

According to the present invention, the above-mentioned aspects of the present invention can be accomplished.

Specifically, since the optical characteristics adjusting system for sunglasses or goggles includes lenses formed of LCD panels, a drive unit applying a drive voltage to the LCD panels, and a control unit configured to output a control signal to the drive unit, adjustment of the optical transmittance and/or color of the lenses becomes possible.

In addition, since the optical characteristics adjusting system for sunglasses or goggles includes a temperature detecting sensor, compensation of a variation in temperature becomes possible.

Further, since the optical characteristics adjusting system for sunglasses or goggles includes an illuminance detecting sensor, optical transmittance of lenses according to a variation in illuminance can be optimally and rapidly adjusted.

Furthermore, since a wearing detecting sensor is provided, driving of the lenses upon non-wearing can be stopped, and thus power consumption can be minimized.

DESCRIPTION OF DRAWINGS

The above and other aspects and advantages of the present invention will become apparent and more readily appreciated from the following description of exemplary embodiments, taken in conjunction with the accompanying drawings of which.

MODE FOR INVENTION

Reference will now be made in detail to the embodiments of the present invention, examples of which are illustrated in the accompanying drawings. However, it will be apparent to those skilled in the art that the following embodiments can be readily understood and modified into various types, and the scope of the present invention is not limited to the embodiments.

Configurations and operations of embodiments according to the present invention will be described with reference to the accompanying drawings.

Figure 1:
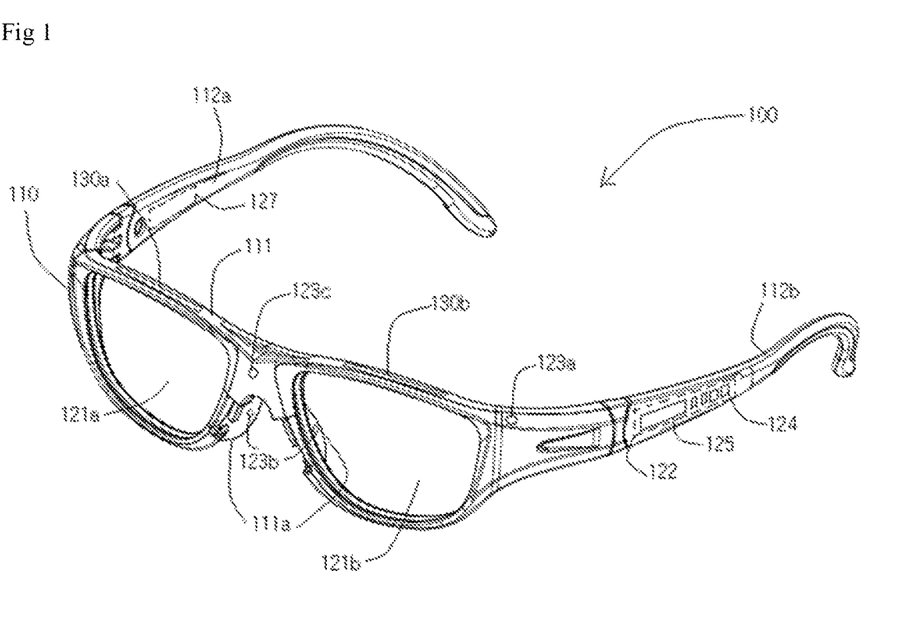
FIG. 1 is a perspective view of sunglasses according to an embodiment of the present invention.

FIG. 1 shows sunglasses according to an embodiment of the present invention. Referring to FIG. 1, sunglasses 100 include a sunglasses frame 110, and an optical characteristics adjusting system for sunglasses 120. The sunglasses 100 can perform selection of lens color and/or automatic adjustment of optical transmittance by the optical characteristics adjusting system 120.

The sunglasses frame 110 includes a body section 111, and first and second leg sections 112a and 112b. The body section 111 includes a nose pad 111a disposed in front of a wearer's eyes when the wearer wears the sunglasses. The first and second leg sections 112a and 112b are portions disposed at left and right sides of the wearer's head upon wearing, which are hinged at both sides of the body section 111 to be folded or spread with respect to the body section 111.

Figure 2:
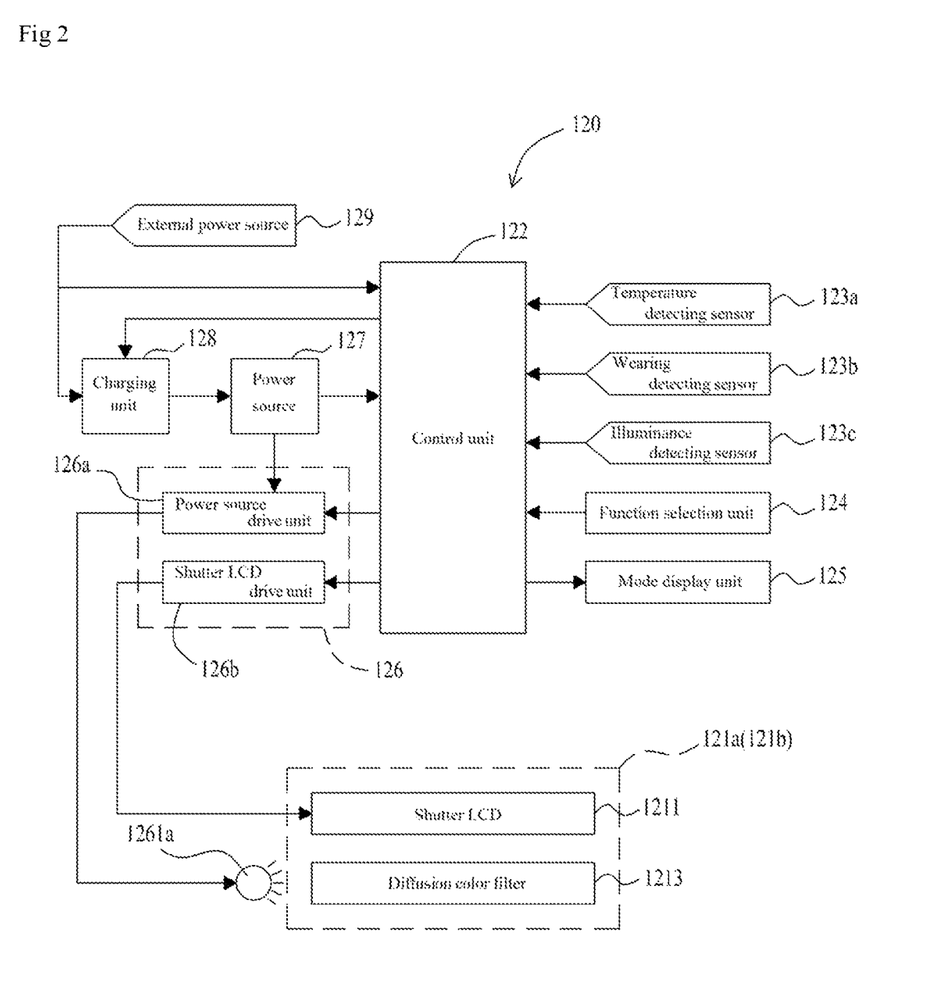
FIG. 2 is a block diagram of an optical characteristics adjusting system for sunglasses according to a first embodiment of the present invention.

FIG. 2 shows an optical characteristics adjusting system for sunglasses according to a first embodiment of the present invention. Referring to FIG. 2, the optical characteristics adjusting system for sunglasses 120 includes lenses 121a and 121b, a control unit 122, a temperature detecting sensor 123a, a wearing detecting sensor 123b, an illuminance detecting sensor 123c, a function selection unit 124, a mode display unit 125, a lens drive unit 126, the light source unit 1261a, a power source 127, and a charging unit 128.

Figure 3:
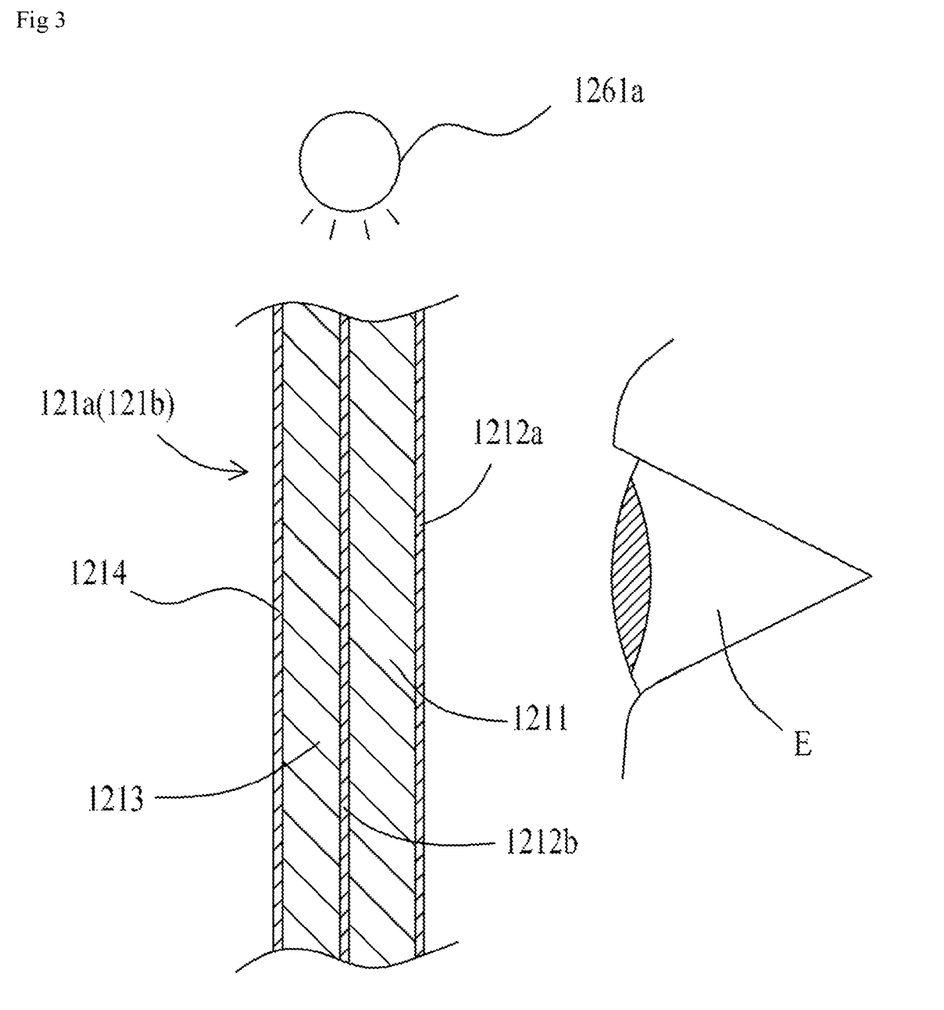
FIG. 3 is a cross-sectional view of a lens shown in FIG. 2.

As shown in FIG. 1, the lenses 121a and 121b are fixed to the body section 111 of the sunglasses frame 110. FIG. 3 is a cross-sectional view of the lens 121a (121b). Referring to FIG. 3, the lens 121a (121b) includes an LCD panel 1211, first and second polarizing films 1212a and 1212b disposed at both surfaces of a shutter LCD 1211, a diffusion color filter 1213 disposed opposite to the shutter LCD 1211 with the second polarizing film 1212b interposed therebetween, and a harmful ray filter 1214 disposed opposite to the second polarizing film 1212b with the diffusion color filter 1213 interposed therebetween.

The LCD panel 1211 is a shutter LCD configured to enable an optical transmittance adjustment according to a magnitude of a drive voltage. The magnitude of the drive voltage applied to the LCD panel 1211 for the purpose of optical transmittance adjustment is adjusted by the lens drive unit 126. That is, a concentration of the lenses 121a and 121b is adjusted by the LCD panel 1211. In the embodiment, the LCD panel 1211 will be described as a flexible plastic LCD.

The diffusion color filter 1213 represents a color of the lenses 121a and 121b, and the color of the light source unit 1261a is diffused in the diffusion color filter 1213 to determine the color of the lenses 121a and 121b.

While not shown, the control unit 122 may be provided as a microcomputer including a memory device in which a control program is stored, and a central processing unit (CPU) for performing the control program. In the embodiment, as shown in FIG. 1, the control unit 122 is described as being installed in the second leg section 112b of the sunglasses frame 110 but the present invention is not limited thereto. The control unit 122 receives power from the power source 127, ambient temperature data from the temperature detecting sensor 123a, information about whether the wearer wears the sunglasses from the wearing detecting sensor 123b, and ambient illuminance data from the illuminance detecting sensor 123c. In addition, the control unit 122 receives function selection information such as automatic adjustment and manual adjustment of a concentration, or the like, from the function selection unit 124. The control unit 122 outputs a control signal to the lens drive unit 126, and outputs information about a current status to the mode display unit 125. The control unit 122 receives power from the power source 127 provided therein and an external power source 129. The control unit 122 will be described below in detail with reference to FIG. 4.

The temperature detecting sensor 123a detects a temperature around the sunglasses 100 to transmit the temperature data to the control unit 122. In the embodiment, as shown in FIG. 1, the temperature detection sensor 123a is described as being disposed at one side of the body section 111 of the sunglasses frame 110 but the present invention is not limited thereto. For example a thermistor may be used as the temperature detecting sensor 123a.

The wearing detecting sensor 123b detects a wearing state of the sunglasses 100 and transmits the information to the control unit 122. In the embodiment, as shown in FIG. 1, the wearing detecting sensor 123b is described as a light sensor installed at the nose pad 111a of the body section 111 of the sunglasses frame 110 but the present invention is not limited thereto. In this case, the wearing state is determined according to a light detecting state of the wearing detecting sensor 123b.

The illuminance detecting sensor 123c detects an illuminance around the sunglasses 100 and transmits the data to the control unit 122. In the embodiment, as shown in FIG. 1, the illuminance detecting sensor 123c is described as being installed at a center of the body section 111 of the sunglasses frame 110 but the present invention is not limited thereto.

The function selection unit 124 allows a user of the sunglasses 100 to select whether the user selects the color, whether the concentration is adjusted through automatic adjustment or manual adjustment, or the like. In the embodiment, as shown in FIG. 1, the function selection unit 124 is described as being installed at the second leg section 112b of the sunglasses frame 110 but the present invention is not limited thereto.

The mode display unit 125 is a display device such as an LCD, which receives data about a current state from the control unit 122 to output the data. The information that can be displayed on the mode display unit 125 may be a concentration, a color, a battery residual value, and so on. In the embodiment, as shown in FIG. 1, the mode display unit 125 is described as being installed at the second leg section 112b of the sunglasses frame 110 but the present invention is not limited thereto.

The lens drive unit 126 includes a light source drive unit 126a and a shutter LCD drive unit 126b. The lens drive unit 126 receives a control signal from the control unit 122, and drives the shutter LCD 1211 of the lenses 121a and 121b and the light source unit 1261a according thereto. The light source drive unit 126a is configured to allow the light source unit 1261a to radiate light having a selected color based on the control signal input from the control unit 122. The shutter LCD drive unit 126b adjusts an operating voltage such that the shutter LCD 1211 has an appropriate optical transmittance (concentration) based on the control signal input from the control unit 122. The shutter LCD drive unit 126b generates an operating voltage having a frequency of 36 Hz or less (preferably, 1 Hz or less) to reduce power consumption. The lens drive unit 126 receives power from the power source 127.

The power source 127 supplies power to the control unit 122, the lens drive unit 126, and so on. In the embodiment, the power source 127 is described as being constituted by a secondary battery, which is rechargeable, but the present invention is not limited thereto. The charging unit 128 is controlled by the control unit 122, and the power source 127 is stably charged from the external power source 129. In the embodiment, as shown in FIG. 1, the power source 127 and the charging unit 128 are described as being installed at the first leg section 112a of the sunglasses frame 110 but the present invention is not limited thereto. In addition, the power source 127 may employ a primary battery instead of the secondary battery. Further, solar batteries 130a and 130b installed at the sunglasses frame 110 may be connected to the power source 127 and used.

Figure 4:
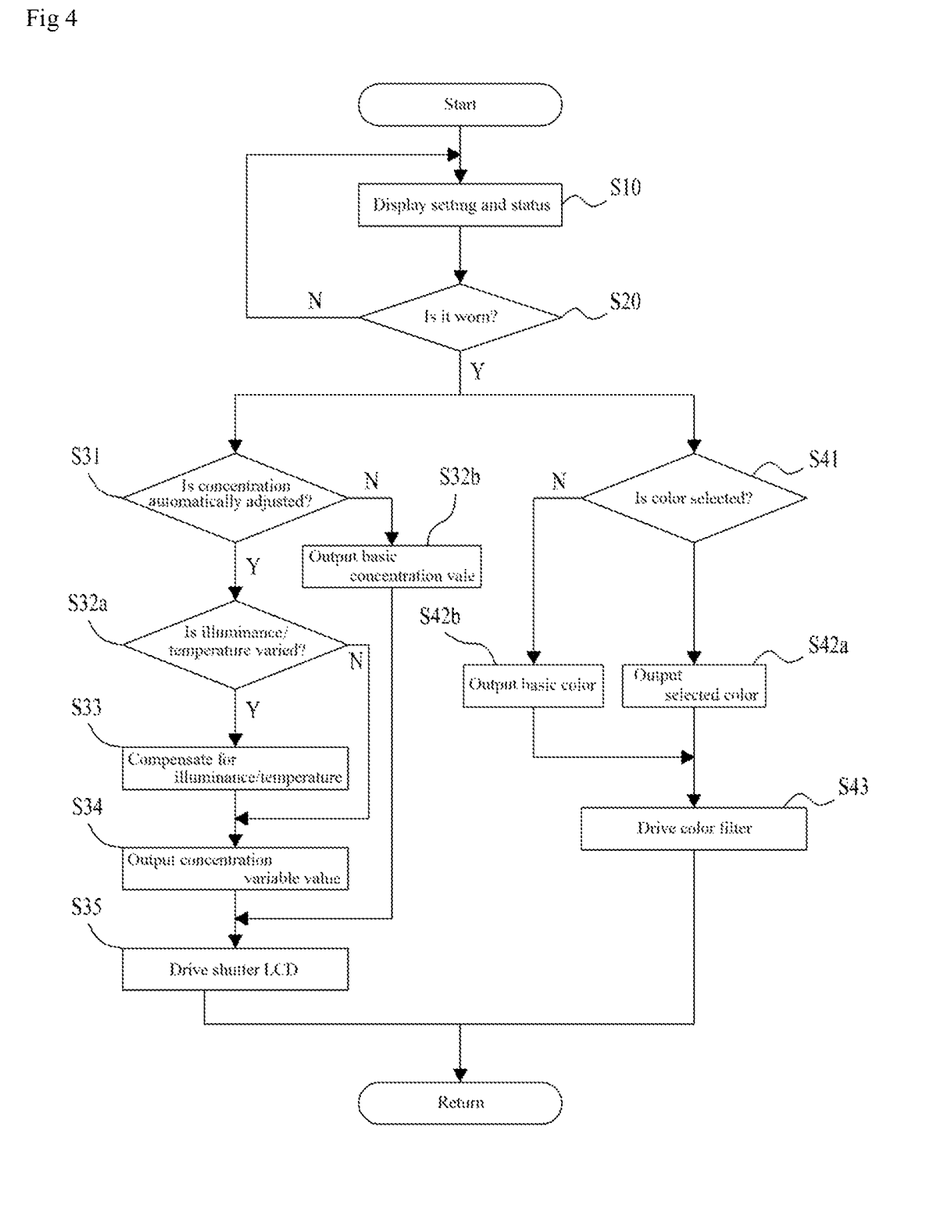
FIG. 4 is a flowchart for describing an operation of the optical characteristics adjusting system for sunglasses shown in FIG. 2.

FIG. 4 shows a flowchart for describing an operation of the optical characteristics adjusting system for sunglasses shown in FIG. 2. Hereinafter, an operation of the optical characteristics adjusting system for sunglasses shown in FIG. 2 will be described in detail with reference to FIG. 4.

First, a display of a setting and mode is performed regardless of a wearing state (S10). In this step, a battery residual value or the like is displayed through the mode display unit 125.

Next, the wearing state is checked (S20). Checking of the wearing state is performed by allowing the wearing detecting sensor 123b (see FIGS. 1 and 2) to detect whether the user wears the sunglasses, transmitting the result to the control unit 122, and allowing the control unit 122 to determine whether the user wears the sunglasses. When it is determined that the user does not wear the sunglasses (N), the display step (S10) of the setting and status is performed again. When it is determined that the user wears the sunglasses (Y), processes of concentration adjustment (optical transmittance adjustment) and color selection are simultaneously performed.

First, the concentration adjustment process will be described. The concentration adjustment process includes a function selection identification step (S31), an illuminance/variation in temperature identification step (S32a), an illuminance/temperature compensation step (S33), a concentration variable value output step (S34), a shutter LCD driving step (S35), and a basic concentration value output step (S32b). The function selection identification step (S31) is a step of checking whether the user selects an automatic concentration adjustment function, which is performed through the function selection unit 124 (FIGS. 1 and 2). When the automatic concentration adjustment function is not selected (N), the basic concentration value output step (S32b) is performed. In the basic concentration value output step (S32b), the control unit 122 (FIGS. 1 and 2) outputs a control signal to the shutter LCD drive unit 126b (FIG. 2) to output a predetermined basic concentration value. Here, the basic concentration value may be one or more. For example, the basic concentration value may be manually selected as one of three stages (bright, medium, and dark). After the basic concentration value output step (S32b), the shutter LCD drive step (S35) is performed.

When the automatic concentration adjustment function is selected (Y), the illuminance/variation in temperature identification step (S32a) is performed. The illuminance/variation in temperature identification step (S32a) is performed by allowing the control unit 122 to receive a related signal from the temperature detecting sensor 123a and the illuminance detecting sensor 123c to determine whether the current illuminance and/or temperature is different from the former value. Upon automatic concentration adjustment, the automatic concentration adjustment of three stages or more becomes possible. Here, light transmissivity may be gradationally set from 3.2% to 99%. When at least one of differences in illuminance and temperature occurs (Y), the illuminance/temperature compensation step (S33) is performed. The illuminance/temperature compensation step (S33) is performed by allowing the control unit 122 to calculate a new control value to compensate the difference in illuminance and/or temperature.

In general, a minimum time that an optic nerve of a human determines an instant variation of ambient illuminance is about 20 mS as an average. When the optic nerve detects the variation in illuminance, an opening level of the pupil is adjusted to cause a reaction of a human body to reduce a fatigue of eyes. A reaction termination time of the pupil differs from individual to individual, for example, 0.1 to several seconds. A time from detection of the variation in illuminance by the optic nerve to completion of the reaction of the pupil results in fatigue of the eyes. Accordingly, before the optic nerve determines the varied ambient illuminance, the control unit 122 determines the signal input from the illuminance detecting sensor 123c to compensate the concentration of the lens to correspond to the varied illuminance. A shielding concentration and the reaction time of the shutter LCD 1211 are varied according to the temperature. That is, as the temperature is lowered, the shielding concentration and the reaction speed of the shutter LCD 1211 are reduced. Accordingly, in order to obtain the concentration and the reaction speed required by the shutter LCD 1211, compensation for the temperature is needed, and the compensation is accomplished in the illuminance/temperature compensation step (S33).

In the concentration variable value output step (S34), the compensation is performed as the control unit 122 outputs the control signal to the shutter LCD drive unit 126*b* based on the compensated illuminance/temperature data. When there is no variation in illuminance and temperature in the illuminance/variation in temperature identification step (S32*a*) (N), the concentration variable value output step (S34) is performed immediately.

The shutter LCD driving step (S35) is performed as the concentration shutter LCD drive unit 126*b* applies a drive voltage to the shutter LCD 1211.

Next, a color selection process will be described. The color selection process includes a color selection determination step (S41), a selected color output step (S42*a*), a basic color output step (S42*b*), and a color filter drive step (S43).

The color selection determination step (S41) is a step of determining whether a user selects a desired color, which is performed by the function selection unit 124 (FIGS. 1 and 2). When the color is not selected (N), the basic color output step (S42*b*) is performed. In the basic color output step (S42*b*), the control unit 122 (FIGS. 1 and 2) outputs a control signal to the light source drive unit 126*a* to output a predetermined basic color.

When the wearer selects the color (Y), the selected color output step (S42*a*) is performed. In the selected color output step (S42*a*), the control unit 122 (FIGS. 1 and 2) outputs a control signal to the light source drive unit 126*a* so that the light source unit 1261*a* radiates the color selected by the wearer. The color filter driving step (S43) is performed as the light source drive unit 126*a* applies a drive voltage to the light source unit 1261*a* according to the control signal from the control unit 122.

Figure 5:
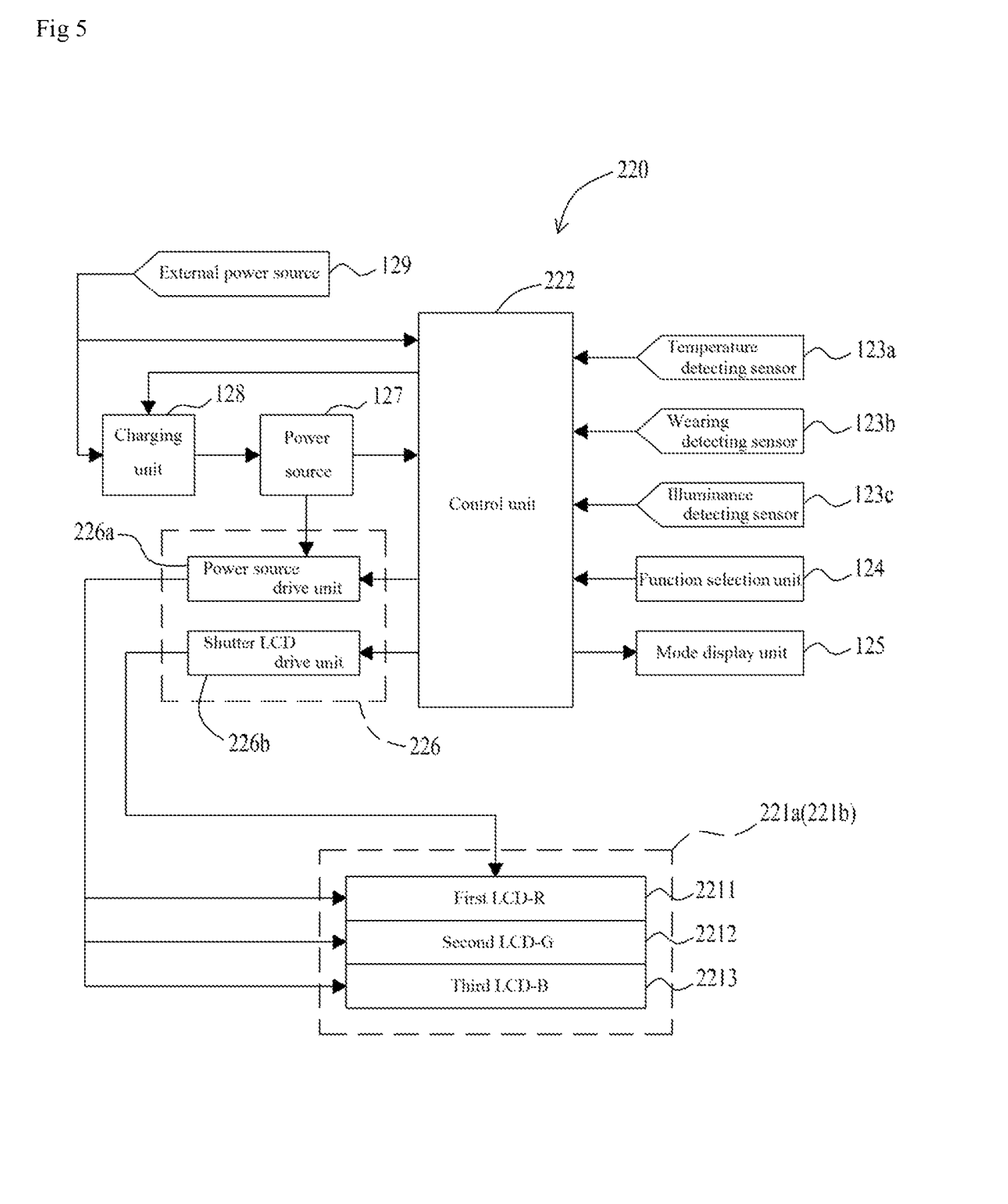
FIG. 5 is a block diagram of an optical characteristics adjusting system for sunglasses according to a second embodiment of the present invention.

FIG. 5 shows an optical characteristics adjusting system for sunglasses according to a second embodiment of the present invention. Referring to FIG. 5, an optical characteristics adjusting system for sunglasses 220 includes lenses 221*a* and 221*b*, a control unit 222, a temperature detecting sensor 123*a*, a wearing detecting sensor 123*b*, an illuminance detecting sensor 123*c*, a function selection unit 124, a mode display unit 125, a lens drive unit 226, a power source 127 and a charging unit 128. Since the components other than the lenses 221*a* and 221*b*, the control unit 222 and the lens drive unit 226 are the same as in the first embodiment shown in FIG. 2, only the lenses 221*a* and 221*b*, the control unit 222 and the lens drive unit 226 will be described below.

Figure 6:
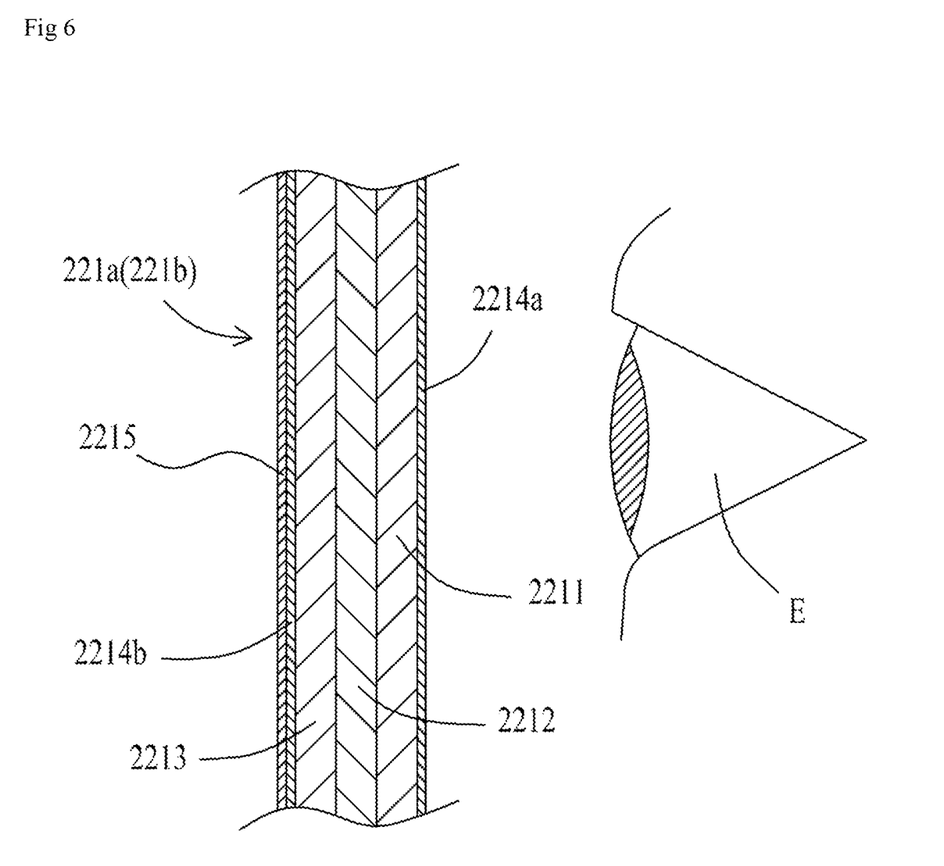
FIG. 6 is a cross-sectional view of a lens shown in FIG. 5.

FIG. 6 shows a cross-sectional view of the lens 221*a* (221*b*). Referring to FIG. 6, the lens 221*a* (221*b*) includes a first LCD panel 2211, which is red, a second LCD panel 2212, which is green, stacked on the first LCD panel 2211, a third LCD panel 2213, which is blue, stacked on the second LCD panel 2212 and opposite to the first LCD panel 2211, a first polarizing film 2214*a* formed on an outer surface of the first LCD panel 2211, a second polarizing film 2214*b* formed on an outer surface of the third LCD panel 2213, and a harmful ray filter 2215 formed on an outer surface of the second polarizing film 2214*b*. The respective LCD panels 2211, 2212 and 2213 are driven by the lens drive unit 226 to adjust the color and optical transmittance.

The control unit 222 may be provided as a microcomputer including a memory device in which a control program is stored, and a central processing unit (CPU) for performing the control program, which are not shown, respectively. The control unit 222 receives power from the power source 127, ambient temperature data from the temperature detecting sensor 123*a*, information about whether the wearer wears the sunglasses from the wearing detecting sensor 123*b*, and ambient illuminance data from the illuminance detecting sensor 123*c*. In addition, the control unit 222 receives function selection information such as automatic adjustment and manual adjustment of a concentration, or the like, from the function selection unit 124. The control unit 222 outputs a control signal to the lens drive unit 226, and outputs information about a current status to the mode display unit 125. The control unit 222 receives power from the power source 127 provided in itself and an external power source 129. The control unit 222 will be described below in detail with reference to FIG. 7.

The lens drive unit 226 includes a distribution ratio adjustment unit 226*a*, and an electric current flowing time adjustment unit 226*b*. The lens drive unit 226 receives the control signal from the control unit 222 to drive the respective LCD panels 2211, 2212 and 2213 of the lenses 221*a* and 221*b* according thereto. The distribution ratio adjustment unit 226*a* adjusts a distribution ratio of signals output to the LCD panels 2211, 2212 and 2213 to adjust the color of the lenses 221*a* and 221*b*. The electric current flowing time adjustment unit 226*b* adjusts an electric current flowing time of the signals periodically output to the LCD panels 2211, 2212 and 2213 to adjust optical transmittance of the lenses 221*a* and 221*b*. A concentration of the lenses 221*a* and 221*b* is in proportion to the electric current flowing time of the signals periodically output to the LCD panels 2211, 2212 and 2213. The lens drive unit 226 receives power from the power source 127.

Figure 7:
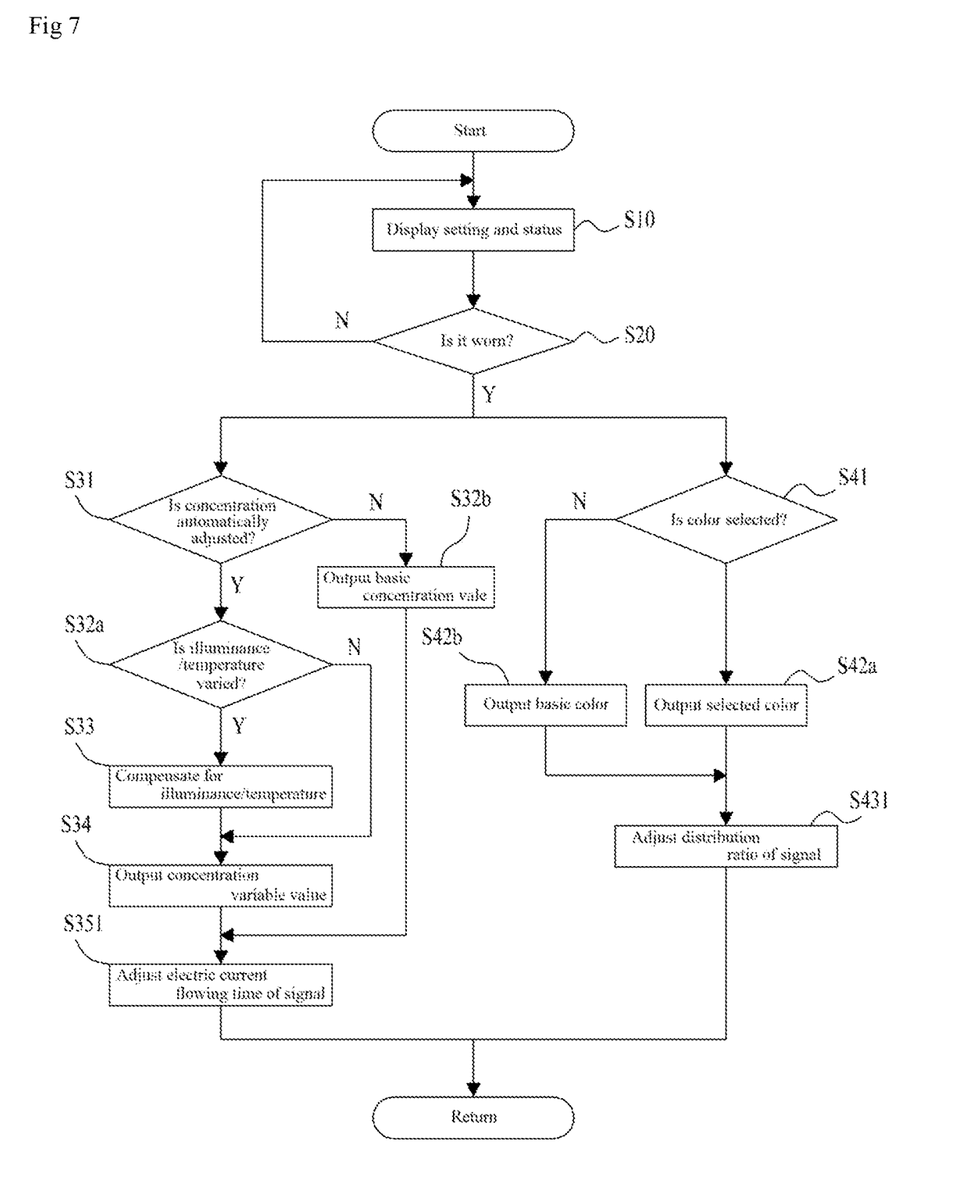
FIG. 7 is a flowchart for describing an operation of the optical characteristics adjusting system for sunglasses shown in FIG. 5.

FIG. 7 shows a flowchart for describing an operation of the optical characteristics adjusting system for sunglasses shown in FIG. 5. Referring to FIG. 7, since the operation is the same as in the description of FIG. 4 except for an electric current flowing time adjustment step (S351) of a signal for concentration adjustment and a distribution ratio adjustment step (S431) of a signal for color selection, detailed description thereof will be omitted.

Figure 8:
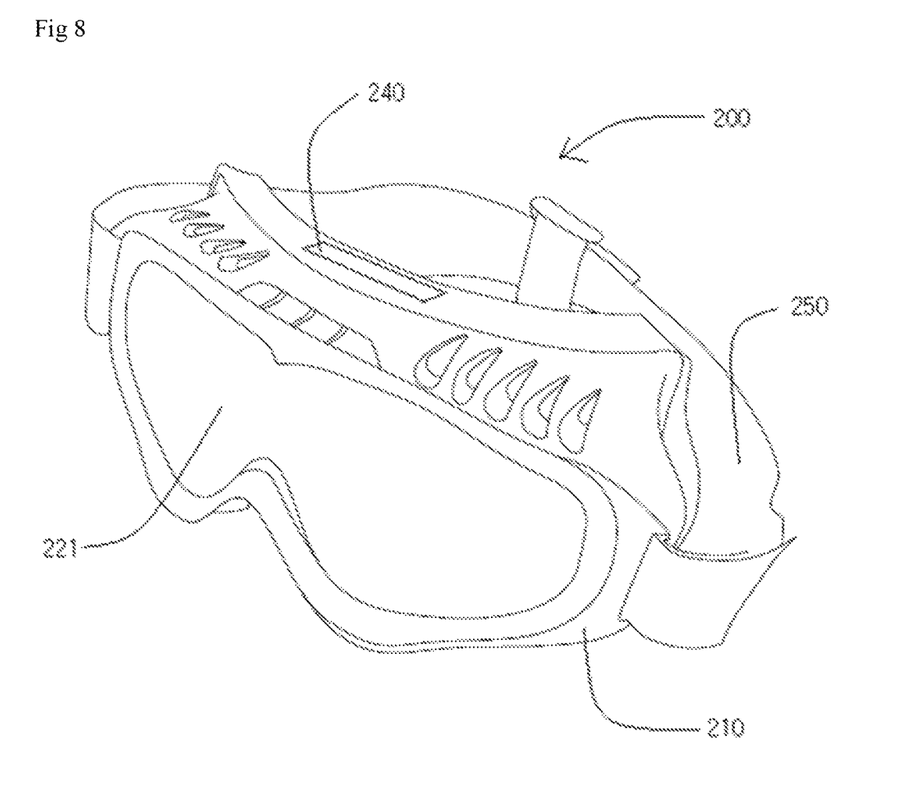
FIG. 8 is a perspective view of goggles according to another embodiment of the present invention.

While the optical characteristics adjusting system according to the present invention has been described as being used for the sunglasses of the embodiment, the present invention is not limited thereto. It will be apparent to those skilled in the art that, as shown in FIG. 8, the optical characteristics adjusting system according to the present invention can also be applied to goggles 200 including a frame 210, a lens 221, a solar battery 240 and a band 250, which also fall into the scope of the present invention.

The foregoing description concerns an exemplary embodiment of the invention, is intended to be illustrative, and should not be construed as limiting the invention. The present teachings can be readily applied to other types of devices and apparatuses. Many alternatives, modifications, and variations within the scope and spirit of the present invention will be apparent to those skilled in the art.

The invention claimed is:

1. An optical characteristics adjusting system for sunglasses or goggles comprising:
   a lens equipped with an LCD panel;
   a lens drive unit equipped with an LCD driving unit for applying a drive voltage to the LCD panel;

an illuminance detecting sensor for detecting an ambient illuminance;
a wearing detecting sensor for providing information about a wearing state of the sunglasses to the control unit;
a solar battery positioned in a portion of a frame above each lens;
a function selection unit in a leg section of a frame of the sunglasses or goggles for selecting automatic adjustment and manual adjustment of optical transmittance of the lens;
a control unit for controlling an operation of the lens drive unit according to a signal from the illuminance detecting sensor and for adjusting the lens in response to ambient illuminance; and
a light source unit for emitting light having one or more colors and being configured to alternate between a plurality of colors,
wherein the lens further comprises a diffusion color filter for receiving light from the light source unit, and the lens drive unit comprises a light source drive unit for driving the light source unit,
wherein the control unit outputs a control signal to the light source drive unit such that the light source unit radiates a selected color of the plurality of colors,
wherein the wearing detecting sensor is a light sensor positioned on a nose pad of the sunglasses or goggles and determines a wearing state according to a light detecting state of the wearing detecting sensor; and
wherein the control unit is disposed in a leg section of a frame of the sunglasses or goggles.

2. The optical characteristics adjusting system for sunglasses or goggles according to claim 1, wherein the LCD panel is a shutter LCD equipped with optical transmittance adjusted by the LCD drive unit.

3. The optical characteristics adjusting system for sunglasses or goggles according to claim 1, wherein the lens comprises a first LCD panel, which is red, a second LCD panel, which is green, and a third LCD panel, which is blue, and
the LCD drive unit comprises an electric current flowing time adjustment unit for adjusting an electric current flowing time of signals periodically output to the three LCD panels, and a distribution ratio manipulation unit for adjusting a distribution ratio of the signals output to the three LCD panels.

4. The optical characteristics adjusting system for sunglasses or goggles according to claim 1, further comprising a temperature detecting sensor for providing ambient temperature data to the control unit,
wherein the control unit outputs the control signal compensated with respect to the ambient temperature to the LCD drive unit.

5. The optical characteristics adjusting system for sunglasses or goggles according to claim 1, wherein the drive voltage of the LCD panel has a frequency of 36 Hz or less.

6. The optical characteristics adjusting system for sunglasses or goggles according to claim 1, wherein the drive voltage of the LCD panel has a frequency of 1 Hz or less.

7. The sunglasses comprising the optical characteristics adjusting system according to claim 1.

8. The goggles comprising the optical characteristics adjusting system according to claim 1.

9. An optical characteristics adjusting system for sunglasses or goggles comprising:
a lens equipped with an LCD panel;
a lens drive unit equipped with an LCD driving unit for applying a drive voltage to the LCD panel;
an illuminance detecting sensor for detecting an ambient illuminance;
a wearing detecting sensor for providing information about a wearing state of the sunglasses to the control unit;
a solar battery positioned in a portion of a frame above a top of each lens;
a function selection unit in a leg section of a frame of the sunglasses or goggles for selecting automatic adjustment and manual adjustment of optical transmittance of the lens;
a control unit for controlling an operation of the lens drive unit according to a signal from the illuminance detecting sensor and for adjusting the lens in response to ambient illuminance; and
a light source unit for emitting light having one or more colors and being configured to alternate between a plurality of colors,
wherein the lens further comprises a diffusion color filter for receiving light from the light source unit, and the lens drive unit comprises a light source drive unit for driving the light source unit,
wherein the control unit outputs a control signal to the light source drive unit such that the light source unit radiates a selected color of the plurality of colors,
wherein the wearing detecting sensor is a light sensor positioned on a nose pad of the sunglasses or goggles and determines a wearing state according to a light detecting state of the wearing detecting sensor; and
wherein the control unit is disposed in a leg section of a frame of the sunglasses or goggles.

10. The optical characteristics adjusting system for sunglasses or goggles according to claim 9, wherein the LCD panel is a shutter LCD equipped with optical transmittance adjusted by the LCD drive unit.

11. The optical characteristics adjusting system for sunglasses or goggles according to claim 9, wherein the lens comprises a first LCD panel, which is red, a second LCD panel, which is green, and a third LCD panel, which is blue, and
the LCD drive unit comprises an electric current flowing time adjustment unit for adjusting an electric current flowing time of signals periodically output to the three LCD panels, and a distribution ratio manipulation unit for adjusting a distribution ratio of the signals output to the three LCD panels.

12. The optical characteristics adjusting system for sunglasses or goggles according to claim 9, further comprising a temperature detecting sensor for providing ambient temperature data to the control unit, wherein the control unit outputs the control signal compensated with respect to the ambient temperature to the LCD drive unit.

13. The optical characteristics adjusting system for sunglasses or goggles according to claim 9, wherein the drive voltage of the LCD panel has a frequency of 36 Hz or less.

14. The optical characteristics adjusting system for sunglasses or goggles according to claim 9, wherein the drive voltage of the LCD panel has a frequency of 1 Hz or less.

15. The sunglasses comprising the optical characteristics adjusting system according to claim 9.

16. The goggles comprising the optical characteristics adjusting system according to claim 9.

* * * * *